United States Patent [19]

Bourquin

[11] Patent Number: 5,472,714
[45] Date of Patent: Dec. 5, 1995

[54] DOUBLE-LAYERED OXCARBAZEPINE TABLETS

[75] Inventor: Jacques Bourquin, Riehen, Switzerland

[73] Assignee: Ciba-Geigy Corporation, Ardsley, N.Y.

[21] Appl. No.: 288,414

[22] Filed: Aug. 10, 1994

[30] Foreign Application Priority Data

Sep. 8, 1993 [CH] Switzerland ............... 2679/93

[51] Int. Cl.[6] ........................................ A61K 9/36
[52] U.S. Cl. .................... 424/472; 424/464; 424/474; 424/480; 427/2.14
[58] Field of Search ................... 424/464, 472, 424/474, 480; 427/2.14

[56] References Cited

U.S. PATENT DOCUMENTS

| | | | |
|---|---|---|---|
| 3,642,775 | 2/1972 | Schindler | 514/217 |
| 3,716,640 | 2/1973 | Schindler | 514/217 |
| 4,409,212 | 10/1983 | Mandadori | 514/217 |
| 4,543,370 | 9/1985 | Porter et al. | 523/100 |
| 4,579,683 | 4/1986 | Schindler | 540/590 |
| 4,849,218 | 7/1989 | Hess et al. | 424/472 |
| 4,931,286 | 6/1990 | Johnson et al. | 424/480 |
| 5,296,233 | 3/1994 | Batista et al. | 424/480 |
| 5,322,698 | 6/1994 | Kovács et al. | 424/480 |
| 5,326,570 | 7/1994 | Rudnic et al. | 424/458 |

OTHER PUBLICATIONS

"R. Voigt" Manual of Pharmaceutical Technology 6th Edition, VCH 1987, ISBN 3-527-26595-3 (p. 162).

*Primary Examiner*—John C. Bleutge
*Assistant Examiner*—Amy L. Hulina
*Attorney, Agent, or Firm*—Karen G. Kaiser

[57] ABSTRACT

The invention relates to color-stable tablets for the therapeutic drug oxcarbazepine, which tablets are provided with a hydrophilic, permeable layer containing white pigments and a hydrophilic, permeable outer layer containing white pigments in combination with iron(II) oxide pigments.

1 Claim, No Drawings

DOUBLE-LAYERED OXCARBAZEPINE TABLETS

The present invention relates to double-layered tablets for the therapeutic drug oxcarbazepine and to a process for the preparation of said tablets.

Oxcarbazepine, 10,11-dihydro-10-oxo-5H-dibenzo[b,f]azepine-5-carboxamide, is regarded, like ®Tegretol [(Ciba-Geigy) carbamazepin: 5H-dibenzo[b,f]azepine- 5-carboxamide], as the therapeutic drug of first choice for the treatment of convulsions and severe painful conditions. The commercially available dosage forms, such as tablets and syrups, are especially suitable for regularly recurring administration over a prolonged period of treatment in order to ensure a uniform concentration of active drug in the blood.

A stability problem arises in connection with tablets containing oxcarbazepine. During storage at room temperature, an inhomogeneous, faintly orange discolouration of the originally white tablet is observed. Investigations have revealed that this unwanted discolouration is caused by the formation of a minor amount (<0.05%) of an oxidation product of the active drug. This oxidation product is presumed to be diketoiminodibenzyl: 10,11-dihydro-5H-dibenzo[b,f]azepine-10,11-dione. The oxidation product is held in principle to be pharmacologically harmless. But to ensure an external homogeneity of the commercial product for as long as possible, the addition of the pigment, iron(II) oxide (FeO), is made during the compression operation to deal with the inhomogeneous orange dicolouration caused by the oxidation product. The homogeneous yellowish-orange discolouration of the tablets caused by this addition of iron(II) oxide can be tolerated, as no further discolouration of the tablets is observed during storage. Only a very few dyes are pharmacologically acceptable for enteral dosage forms and therefore approved for formulation purposes.

However, even the use of iron(II) oxide as adjunct for the preparation of tablets is problematical. In the USA, the FDA (Food and Drug Administration), which is responsible for drug registration, has called for a restriction of the amount in which the adjunct is added to ensure a permissible daily maximum ingestion of only 5 mg of iron. It is expected that the drug registration authorities in other countries will follow the example of the FDA in requiring this restriction. The reason behind the restriction is the physiological action of iron itself, which is undesirable in a pharmaceutical excipient.

The present invention has for its object to provide colour-stable tablets for the therapeutic drug oxcarbazepine that permit keeping the maximum daily ingestion of iron to 5 mg.

This object is achieved by the present invention, which relates to a double-layered tablet for the therapeutic drug 10,11-dihydro-10-oxo-5H-dibenzo[b,f]azepine-5-carboxamide, which tablet comprises the following ingredients:

a) a tablet core comprising a therapeutically effective dose of 10,11-dihydro-10-oxo- 5H-dibenzo[b,f]azepine-5-carboxamide;

b) a hydrophilic, permeable inner layer containing white pigments and further optional adjuncts, and c) a hydrophilic, permeable outer layer containing white pigments in combination with iron(II) oxide pigments and further optional adjuncts.

The tablets of this invention meet the criteria of storage stability and are distinguished in particular by a colour stability of up to several months. The tablets retain their homogeneous yellowish colouration for a very long time.

A further object of this invention is the process for the preparation of the double-layered tablets for the therapeutic drug 10,11-dihydro-10-oxo-5H-dibenzo[b,f]azepine-5-carboxamide. This process comprises a) compressing the active drug, together with conventional excipients, to a tablet core by standard tabletting methods, and providing said core successively with b) a hydrophilic, permeable inner layer containing white pigments, and c) a hydrophilic, permeable outer layer containing white pigments in combination with iron(II) oxide pigments.

The terms and expressions used throughout this specification are defined as follows within the scope of this invention:

The term "double-layered tablet" denotes a solid dosage form for peroral administration in a single dose, which can be prepared by compressing the therapeutic drug with conventional tabletting adjuncts to a tablet core by means of standard tabletting methods and subsequently coating the cores. A preferred process variant comprises preparing tablet cores by the so-called compacting method (=dry granulation) by compressing the active drug with the adjuncts to larger objects, e.g. coarse lumps, comminuting these by grinding and compressing the grinding stock to tablet cores. The compacting method is described, inter alia, in R. Voigt, Lehrbuch der Pharmazeutischen Technologie (Manual of Pharmaceutical Technology), 6th edition, VCH 1987, ISBN 3-527-26595-3, page 162.

Suitable excipients for compacting methods are preferably those that are suitable for the conventional direct compression processes, for example powder binders such as starch, typically including potato, wheat and corn starch, microcrystalline cellulose, e.g. commercial products obtainable under the registered trademarks Avicel®, Filtrak®, Heweten® or Pharmacel®, highly dispersed silica, e.g. Aerosil®, mannitol, lactose, and also polyethylene glycol, preferably having a molecular mass of 4000 to 6000, crosslinked polyvinyl pyrrolidone (Polyplasdone® XL or Kollidon® CL), crosslinked carboxymethyl cellulose (Acd-isol® CMC-XL), carboxymethyl cellulose [Nymcel®, e.g. ZSB-10, (Nyma)], hydroxypropyl methyl cellulose, e.g. HPMC 603, carboxymethyl starch [Explotab® (Mendell) or Primojel® (Scholtens)], microcrystalline cellulose, e.g. Avicel® PH 102, dicalcium phosphate, e.g. Emcompress® or talcum. The addition of minor amounts of lubricants such as magnesium stearate is also advantageous.

Further suitable excipients are ultraamylopectin, siliconised talcum, aluminium stearate, stearic acid, palmitic acid, skimmed milk powder, stearyl, cetyl and myristyl alcohol, Lanette® O, paraffin or hydrogenated fats. Attention is drawn in this connection to the comprehensive technical literature on the subject.

The conventional wet grinding process is therefore also suitable, comprising blending fillers such as starch, microcrystalline cellulose, lactose, glucose, mannitol, talcum, dextrin or alginate with binders such as polyvinyl pyrrolidone, gelatin, gum arabic, tragacanth or acacia gum, and adding an aqueous solution of ethanol to the mixture. The moist mixture is kneaded, the solvent is removed by drying, and the granulate is compressed in a tabletting machine to tablet cores with the optional addition of flow regulators, lubricants or mould release agents.

The therapeutic drug 10,11-dihydro-10-oxo-5H-dibenzo[b,f]azepine-5-carboxamide is known. Its preparation and the therapeutic use thereof as anticonvulsive drug is described in German Auslegeschrift 20 11 087. An industrially useful process for the preparation of this drug is described in European patent application 0 028 028. Commercially available dosage forms are provided for peroral administration, conveniently tablets containing 300 and 600 mg of active drug. These dosage forms are known under the registered trademark ®Trileptal (Ciba-Geigy) and have been introduced in numerous countries including Denmark, Finland, Austria, Belgium. The introduction of, inter alia, a syrup in further countries is imminent.

Tablet cores are formed by compressing the objects previously ground, e.g. coarse lumps, or granulates, e.g. wet granulates, in conventional tabletting machines such as the Korsch EK-0 eccentric tabletting machine, preferably at a compression force greater than 10 Kn. The tablet cores may vary in shape and be, for example, circular, oval, oblong, cylindrical and the like, and may also vary in size depending on the concentration of therapeutic drug.

The hydrophilic permeable inner layer b) consists of a film-forming material that is permeable to water or gastric juice and is swellable, or at least partially soluble, in these fluids.

Film-foraging materials that are permeable to water are typically hydrophilic mixtures of polyvinyl pyrrolidone or a copolymer of polyvinyl pyrrolidone and polyvinyl acetate with hydroxypropyl methyl cellulose, mixtures of shellac with hydroxypropyl methyl cellulose, polyvinyl acetate or its copolymers with polyvinyl pyrrolidone, or mixtures of water-soluble cellulose derivatives such as hydroxypropyl methyl cellulose, and water-insoluble ethyl cellulose.

These actual coating agents can, if desired, be in admixture with other additional excipients such as talcum or silicon dioxide, e.g. synthetic amorphous silicic acid of the Syloid® (Grace) type, e.g. SYLOID 244 FP, or wetting agents, e.g. the polyethylene glycols or sorbates referred to previously.

Elastic film-like materials are preferably hydrophilic, partially etherified cellulose derivatives.

Hydrophilic, partially etherified cellulose derivatives are typically lower alkyl ethers of cellulose having an average molar degree of substitution (MS) greater than one and smaller than three and having an average degree of polymerisation of c. 100–5000.

The degree of substitution is an indicator of the substitution of the hydroxyl groups per glucose unit by lower alkoxy groups. The average molar degree of substitution (MS) is a mean value and indicates the number of lower alkoxy groups per glucose unit in the polymer.

The average degree of polymerisation (DP) is also a mean value and indicates the average number of glucose units in the cellulose polymer.

Lower alkyl ethers of cellulose typically include cellulose derivatives that are substituted at the hydroxymethyl group (primary hydroxyl group) of the glucose unit forming the cellulose chains and, where appropriate, at the second and third secondary hydroxyl group by $C_1$–$C_4$alkyl groups, preferably methyl or ethyl groups, or by substituted $C_1$–$C_4$alkyl groups, e.g. 2-hydroxyethyl, 3-hydroxy-n-propyl, carboxymethyl or 2-carboxyethyl.

Suitable lower alkyl ethers of cellulose are preferably cellulose derivatives that are substituted at the hydroxymethyl group (primary hydroxyl group) of the glucose unit by $C_1$–$C_4$alkyl groups or by substituted $C_1$–$C_4$alkyl groups, and at the second and, where appropriate, third secondary hydroxyl group by methyl or ethyl groups.

Suitable lower alkyl ethers of cellulose are in particular methyl cellulose, ethyl cellulose, methyl hydroxyethyl cellulose, methyl hydroxypropyl cellulose, ethyl hydroxyethyl cellulose, hydroxyethyl cellulose, hydroxypropyl cellulose, carboxymethyl cellulose (in salt form, e.g. as sodium salt) or methyl carboxymethyl cellulose (also in salt form, e.g. as sodium salt).

Preferred lower alkyl ethers of cellulose are ethyl cellulose (DP: c. 150–1000, MS: c. 1.2–1.8), e.g. of the Aquacoat® (FMC Corp.) type, hydroxyethyl cellulose (DP: c. 120–1200, MS: c. 1.2–2.5) and hydroxypropyl cellulose (DP: c. 200–3000, MS: c. 1.0–3.0).

Further film-forming materials that are permeable to water are cellulose acetate trimellitate (CAT) or the methacrylic acid-methacrylate 1:1 or 1:2 copolymer, e.g. EUDRAGIT L and S, conveniently EUDRAGIT L 12.5 or S 12.5.

The film-forming material is sprayed on to the tablet cores in the form of an aqueous dispersion of redispersible cellulose acetate phthalate—CAP—(Aquateric®:FMC), polyvinyl acetate phthalate—PVAP—(Coateric®:Colorcon), hydroxypropyl methyl cellulose phthalate—HPMCP (Aquacoat® HP 50 or HP 55: Shin-Etsu) as well as, preferably, an acrylic acid-methacrylic acid copolymer which is partially esterified with $C_1$–$C_4$alkyl groups.

An acrylic acid-methacrylic acid 1:1 copolymer which is partially esterified with methyl and/or ethyl groups of the EUDRAGIT L 30 D type or aqueous dispersed EUDRAGIT L 100-55 is also used.

The film-forming materials may contain additional adjuncts such as plasticisers, e.g. triethyl citrate, e.g. Citroflex® (Pfizer), triacetin, various phthalates, e.g. diethyl or dibutyl phthalate, mixed mono- or diglycerides of the Myvacet® (Eastman) type, e.g. MYVACET 9-40, the polyethylene glycols referred to above, e.g. having a relative molar mass of c. 6000–8000 as well as ethylene oxide-propylene oxide block copolymers of the Pluronic® (BASF) or Synperonic® (ICI) type, powdered lubricants such as magnesium trisilicate, starch or synthetic amorphous silicic acid of the SYLOID type, e.g. SYLOID 244 FP.

The hydrophilic permeable inner layer b) contains white pigments, preferably titanium dioxide pigments.

Coating the tablet cores with the hydrophilic permeable coating material is effected in per se known manner by means of standard coating methods.

Typically, the coating material is dissolved or suspended in the desired ratio in water. If desired, an adjunct such as polyethylene glycol is added. This solution or dispersion is sprayed together with other adjuncts, e.g. talcum or silica, e.g. SYLOID 244 FP, by known methods such as spray coating in a fluidised bed using the Aeromatic, Glatt, Wurster or Hüttlin (Kugelcoater) systems, as well as in a coating pan by the methods known as Accela Cota or immersion coating.

It is preferred to spray the tablet cores with an aqueous dispersion containing hydroxypropyl methyl cellulose (cellulose HPMC).

The film-forming coating materials indicated as suitable for the hydrophilic permeable inner layer b) are also suitable for the hydrophilic permeable outer layer c), which contains white pigments such as titanium dioxide or talcum in combination with iron(II) oxide pigments.

As in the case of the inner layer b), it is also preferred to coat the tablet cores with the outer layer c) by spraying them with an aqueous dispersion containing hydroxypropyl methyl cellulose (Cellulose HPMC).

The invention relates preferably to a double-layered tablet for the therapeutic drug 10,11-dihydro-10-oxo-5H-dibenzo [b,f]azepine-5-carboxamide, which tablet comprises the following components:

a) a tablet core comprising a dosage unit of the therapeutic drug 10,11-dihydro- 10-oxo-5H-dibenzo[b,f]azepine- 5-carboxamide;

b) a hydrophilic, permeable inner layer consisting of hydroxypropyl methyl cellulose and polyethylene glycol 8000 containing titanium dioxide pigments, and c) a hydrophilic, permeable outer layer consisting of hydroxypropyl methyl cellulose and polyethylene glycol 8000 containing titanium dioxide pigments in combination with iron(II)oxide pigments.

EXAMPLES

Example 1

| Formulation: | |
|---|---|
| Tablet core | |
| TRILEPTAL (therapeutic drug) | 300.0 mg |
| AEROSIIL 200 (silica aerogel) | 2.5 mg |
| AVICEL PH 102 (microcrystalline cellulose) | 85.0 mg |
| Cellulose HPM 603 (hydroxypropyl methyl cellulose) | 10.0 mg |
| magnesium stearate | 2.5 mg |
| NYMCEL ZSB-10 (modified sodium carboxy methyl cellulose, lower substit.) | 40.0 mg |
| Inner layer | |
| Cellulose HPM 603 (hydroxypropyl methyl cellulose) | c. 6.9 mg |
| polyethylene glycol 8000 | c. 1.2 mg |
| talcum PH | c. 5.0 mg |
| titanium dioxide pigment PH | c. 1.9 mg |
| Outer layer | |
| Cellulose HPM 603 (hydroxypropyl methyl cellulose) | c. 9.2 mg |
| iron oxide yellow 17268 | c. 0.6 mg |
| polyethylene glycol 8000 | c. 1.7 mg |
| talcum PH | c. 6.6 mg |
| titanium dioxide pigment PH | c. 1.9 mg |
| approx. total weight | 475.0 mg |

The therapeutic drug TRILEPTAL and a portion of the magnesium stearate are mixed with the other excipients of the formulation indicated above for the tablet core for 20 minutes in the container mixer. The mixture is compacted to c. 2–6 mm coarse granules having a porosity of c. 17–21% at a compression force of c. 55 kN. The compacted product is then ground to granulates having an average particle size of c. 400 μm. The remaining magnesium stearate is added to this mixture and mixing is continued for a further 10 min. Each matrix is filled with 440 mg of the formulation and processed to tablets having a hardness of c. 125N in a Korsch DSKi 118 eccentric tabletting machine with recording pressure gauge and an oval die 15 mm long and 6.5 mm wide.

The dried tablet cores are afterwards coated in a fluidised bed with the adjuncts listed in the formulation, using as solvent an aqueous ethanolic mixture (11% w/w of ethanol) that additionally contains 5% of isopropanol.

The layered tablet cores are then coated with the outer layer formulation containing the indicated pigments by the same procedure as is used for applying the inner layer.

What is claimed is:

1. A double-layered tablet, comprising:

a) a tablet core containing a dosage unit of the therapeutic drug 10,11-dihydro- 10-oxo-5H-dibenzo[b,f]azepine-5-carboxamide;

b) a hydrophilic, permeable inner layer consisting of hydroxypropyl methyl cellulose and polyethylene glycol 8000 containing titanium dioxide pigments, and c) a hydrophilic, permeable outer layer consisting of hydroxypropyl methyl cellulose and polyethylene glycol 8000 containing titanium dioxide pigments in combination with iron(II)oxide pigments.

* * * * *